United States Patent
Tsuda et al.

(10) Patent No.: US 6,538,165 B1
(45) Date of Patent: *Mar. 25, 2003

(54) PROCESS FOR PRODUCING DIFLUOROMETHANE AND DIFLUOROCHLOROMETHANE

(75) Inventors: Takehide Tsuda; Takashi Shibanuma, both of Osaka (JP)

(73) Assignee: Daikin Industries Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/875,919
(22) PCT Filed: Feb. 8, 1996
(86) PCT No.: PCT/JP96/00264
§ 371 (c)(1),
(2), (4) Date: Jul. 8, 1997
(87) PCT Pub. No.: WO96/24570
PCT Pub. Date: Aug. 15, 1996

(30) Foreign Application Priority Data

Feb. 10, 1995 (JP) ............................................. 7-022595
Nov. 1, 1995 (JP) ............................................. 7-284882

(51) Int. Cl.[7] ............................................. C07C 17/08
(52) U.S. Cl. ..................................................... 570/167
(58) Field of Search ......................................... 570/167

(56) References Cited

U.S. PATENT DOCUMENTS

| | | | |
|---|---|---|---|
| 2,005,711 A | 6/1935 | Daudt et al. | |
| 2,024,095 A | * 12/1935 | Daudt et al. | ................ 570/167 |
| 2,062,743 A | 12/1936 | Daudt et al. | |
| 2,450,414 A | * 10/1948 | Benning | ..................... 570/167 |
| 2,749,374 A | 6/1956 | Ruh et al. | |
| 2,749,375 A | 6/1956 | Ruh et al. | |
| 4,138,355 A | 2/1979 | Ferstandig | |

FOREIGN PATENT DOCUMENTS

| | | |
|---|---|---|
| DE | 1020968 | 5/1958 |
| JP | A59231030 | 12/1984 |
| WO | 09535271 | 12/1995 |

OTHER PUBLICATIONS

Derwent Abstract of SU–1150919–A, published May 15, 1986.

\* cited by examiner

Primary Examiner—Alan Siegel
(74) Attorney, Agent, or Firm—Birch, Stewart, Kolasch & Birch, LLP

(57) ABSTRACT

According to a process for producing difluoromethane and difluorochloromethane, which comprises fluorinating dichloromethane and trichloromethane with hydrogen fluoride in a liquid phase in the presence of a catalyst in one reaction apparatus under the conditions that a reaction pressure is from 1 to 20 kg/cm$^2$ and a reaction temperature is from 50 to 150° C., difluoromethane and difluorochloroethane can be simultaneously or alternatively produced in an economical/safe manner by one reaction apparatus.

20 Claims, 1 Drawing Sheet

PROCESS FOR PRODUCING DIFLUOROMETHANE AND DIFLUOROCHLOROMETHANE

This application is a 371 of PCT/JP96/0064 filed Feb. 8, 1996.

FIELD OF THE INVENTION

The present invention relates to a process for producing difluoromethane and difluorochloromethane, which comprises fluorinating dichloromethane and trichloromethane with hydrogen fluoride in a liquid phase in the presence of a catalyst by one reaction apparatus.

RELATED ART

It is known that difluoromethane (hereinafter referred to as "HFC32") is produced by reacting dichloromethane (hereinafter referred to as "HCC30") with hydrogen fluoride (hereinafter referred to as "HF") in a gas or liquid phase in the presence of a catalyst.

U.S. Pat. Nos. 2,749,374 and 2,749,375 disclose that HCC30 is reacted with HF in a liquid phase at a temperature within the range from 110 to 175° C. in the presence of an antimony chloride fluoride catalyst ($SbCl_xF_y$, x+y=3,y/(x+y)>0.8,Sb(V)>5%) to give HFC32. In this process, however, a large amount of undesired monochloromethane (hereinafter referred to as "HCC40") and fluoromethane (hereinafter referred to as "HFC41"), which are impurities other than HCC30 series and reduce the yield, are generated as by-products. It is also known that HF and antimony halide corrode a material of a reaction apparatus and it is extremely important in the production of HFC32 that the reaction system mixture does not corrode the material of the reaction apparatus. However, the above patents do not disclose that the material of a reactor shows the corrosion resistance in case of reacting under the above conditions. Furthermore, DE1,020,968 discloses that a reactor made of aluminum is used so as to establish the corrosion resistance.

U.S. Pat. No. 4,138,355 discloses that an equimolar amount of antimony trihalide is added to antimony pentahalide for a method for preventing the corrosion of the reactor by a halogen-containing organic compound such as a mixture of HF and antimony pentahalide. In this method, the catalyst is deteriorated with the progress of the reaction and the amount of antimony trihalide increases, which results in change of the catalyst composition. Therefore, it is necessary to cope with it.

Japanese Patent Kokai Publication No. 59-231030 (231030/1984) discloses a process wherein HCC30 is reacted with HF in a gas phase at a reaction temperature of 200° C. by using aluminum fluoride or chromium fluoride as a catalyst to give HFC32. However, it can be said that this process is not an economically advantageous process because the reaction temperature is high (200° C.) and this gas phase reaction requires a complicated apparatus in comparison with the liquid phase reaction.

As a process for producing difluorochloromethane (hereinafter referred to as "HCFC22"), a liquid phase synthesis process using trichloromethane (hereinafter referred to as "HCC20") as a raw material is known (for example, U.S. Pat. Nos. 2,062,743 and 2,024,095).

SUMMARY OF THE INVENTION

An object of the present invention is to solve the above problems in the prior art, thereby providing a process of producing simultaneously or alternatively HFC32 and HCFC22 in an economical/safe manner in one reaction apparatus.

The present inventors have intensively studied various conditions of the process for producing HFC32 and HCFC22, which comprises fluorinating HCC30 and HCC20 with HF in a liquid phase in the presence of a catalyst. As a result, it has been found that there is a region where the respective production conditions are overlapped so that HFC32 and HCFC22 can be produced by using one reaction apparatus. Furthermore, the present inventors have studied the process for obtaining HFC32 and HCFC22 advantageously in view of economy and safety. Thus, the present invention has been accomplished.

The present invention provides a process for producing HFC32 and HCFC22, which comprises reacting HCC30 and HCC20 with HF in a liquid phase in the presence of a fluorinating catalyst in one reaction apparatus, wherein a reaction pressure is from 1 to 20 $kg/cm^2$, and a reaction temperature is within the range from 50 to 150° C. and is a temperature at which hydrogen fluoride is not liquefied under such reaction pressure.

DETAILED DESCRIPTION OF THE INVENTION

Figure 1:
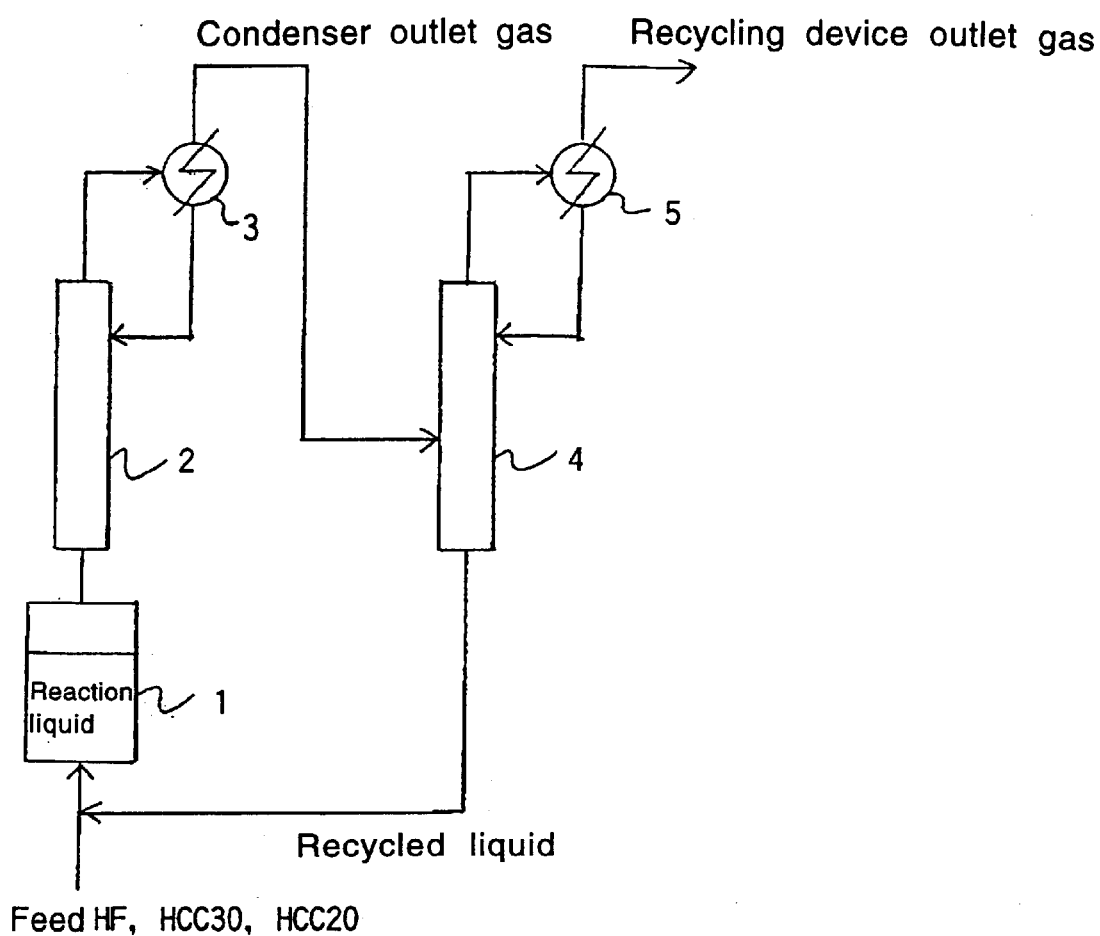
FIG. 1 is a schematically illustrating an apparatus used in Example 1 according to the process of the present invention.

Examples of the fluorinating catalyst used in the process of the present invention include antimony chloride fluoride, titanium chloride fluoride, tin chloride fluoride and the like. A preferred catalyst is antimony chloride fluoride represented by $SbCl_xF_y$ (wherein x+y=5). Antimony chloride fluoride wherein y is from 0.5 to 2 is particularly preferred. If y is smaller than 0.5, the conversion of HCC30 is low and the amount of generated HFC32 per the catalyst is small and, therefore, a large amount of the catalyst is necessary. If y exceeds 2, the conversion of HCC20 is higher and, furthermore, the amount of the undesirable further fluorinated trifluoromethane (hereinafter referred to as "HFC23") increases and the loss amount of HCC20 becomes large so that it can not be said to be economical. Preferably, y is from 0.5 to 1.5.

Antimony chloride fluoride is a chloride fluoride of pentavalent antimony to be formed in situ by partial fluorination of antimony pentachloride. The activity of catalyst is sometimes lost by changing the proportion of x to y with the progress of the reaction. However, it is possible to maintain y within the above range under the conditions of the present invention.

The fluorinating catalyst is used in such an amount that the catalyst is present in the liquid reaction mixture in an amount of 10 to 90% by mol based on the total amount of the liquid reaction mixture and catalyst. If the amount of the catalyst is smaller than 10% by mol, the reaction gas residence time is long and the amount of generated HCC40 and HFC41 increases, which results in poor yield so that it is necessary to conduct sometimes purification. If the amount exceeds 90% by mol, the amount of organic substance decreases and the entrainment amount of the catalyst increases so that clogging of piping is likely to arise unfavorably. The more preferred amount of the catalyst varies depending on the reaction temperature, but is from 40 to 70% by mol.

In the present invention, the catalytic reaction with the catalyst is conducted in the liquid phase. The pressure in the reaction is adjusted to a pressure of 1 to 20 kg/cm². Preferably, it is a pressure of 5 to 10 kg/cm².

The reaction temperature is within the range from 50 to 150° C. and is a temperature higher than that at which HF is not liquefied under the reaction pressure. Preferably, the reaction temperature is a temperature which is at least 3–5° C., e.g. 5° C. higher than the boiling point of hydrogen fluoride under such pressure. If HF is allowed to exist in a liquid state in the liquid reaction mixture, the corrosion resistance of the reactor material is deteriorated so that it is impossible to operate the reaction in safety. In the process of the present invention, HCC30 and HCC20 exist mainly in the liquid state and HF exists mainly in the gas state in the liquid reaction mixture.

According to the preferred embodiment of the present invention, the process of the present invention is conducted by the following steps.

(1) HCC30 and HCC20 are added to a reactor in which a fluorinating catalyst is charged, and they are reacted. The reaction is conducted under the above-mentioned conditions to give HFC32 and HCFC22, and chlorofluoromethane (hereinafter referred to as "HCFC31") and dichlorofluoromethane (hereinafter referred to as "CFC21") which are an intermediate. The reaction can be generally conducted by using a well-known apparatus. The reactor is generally required that starting materials (HCC30 and/or HCC20 and HF) and recycled materials described hereinafter (at least one of HCFC31, HCFC21, HCC30, HCC20 and HF) can be fed in the liquid or gas state and the liquid reaction mixture can be sufficiently heated or cooled. Furthermore, the reactor is required that contact between the reaction materials can be promoted by a suitable mixing method (e.g. installation of stirrer, and an introducing piping). It is necessary that, even if HF is introduced in the liquid state, the temperature can be maintained at the temperature at which HF in the liquid reaction mixture is not liquefied under the predetermined pressure.

(2) Part or all of the reaction mixture is drawn from the reactor. Therefore, the reactor is equipped with a reflux column and a reflux condenser and the reaction mixture is drawn as a reflux condensed liquid or an uncondensed gas. The provision of the reflux column and reflux condenser has an effect of preventing the catalyst from scattering together with the reaction mixture.

(3) The drawn reaction mixture is separated into a mixture of HFC32, HCFC22 and hydrogen chloride as the main reaction product, and a mixture containing at least one of HCC30, HCC20 and HF as other unreacted materials and HCFC31 and HCFC21 as the intermediate. This separation may be conducted by a distillation, because HFC32, HCFC22 and hydrogen chloride have comparatively low boiling point and HCC30, HCC20, HF, HCFC31 and HCFC21 have comparatively high boiling point.

(4) HFC32 and HCFC22 are separated from the mixture consisting of HFC32 and HCFC22 as the main reaction product and hydrogen chloride. In this separation, for example, a conventional process such as distillation and washing with water can be used.

(5) The mixture containing at least one of HCC30, HCC20 and HF as the unreacted material and HCFC31 and HCFC21 as the intermediate is returned to the reactor and reused with circulating.

The above process can also be conducted without circulating the unreacted material, but is preferably conducted by circulating the unreacted material.

The production ratio of HFC32 to HCFC22 in the process of the present invention can be adjusted to an arbitrary production ratio by adjusting the ratio of HCC30 to HCC20 to be fed. In the present invention, HFC32 or HCFC22 can be produced substantially alone.

The molar ratio of HCC30 to HCC20 to be fed may be usually from 0:100 to 100:0 (e.g. 1:100 to 100:1, particularly 50:50). The molar ratio of the amount of HF to the total amount of HCC30 and HCC20 to be fed is from about 2.4:1 to 4:1 in case of the non-cycling operation of the unreacted material and is from about 2:1 to 3:1 in case of the cycling operation of the unreacted material. The time of the contact between the catalyst and raw material in the liquid phase is usually from 0.1 to 10 hours, preferably from 0.5 to 2 hours.

It was conventionally possible to produce HCFC22 by using a material made mainly of iron as the material used in the reactor, but such a material is unfavorable for producing simultaneously HFC32 and HCFC22.

Examples of the preferred material used in the reactor in the process of the present invention include Hastelloy C-22, NAR-25-50MTi, dual-phase stainless steel, SUS-316 and the like. Hastelloy C-22 and NAR-25-50MTi are particularly preferred.

EXAMPLE

The following Examples further illustrate the present invention.

Example 1

Using an apparatus equipped with a 600 mL reactor made of Hastelloy C-22, a reflux column, a reflux condenser and a device for recycling unreacted materials (HCFC31, HCC30, HCFC21, HCC20, HF) to the reactor, the continuous fluorination reaction of HCC30 and HCC20 was conducted.

A schematic diagram of the used apparatus is shown in FIG. 1. The apparatus comprises a reactor 1, a reflux column 2, a reflux condenser 3, a recycling device column 4 and a recycling device condenser 5. The recycling device column 4 and the recycling device condenser 5 form a recycling device. A recycling liquid and fresh HF, HCC30 and HCC20 are fed to the reactor 1.

A catalyst represented by $SbCl_xF_y$ (x+y=5) wherein y is adjusted to 1 was charged in the reactor. A molar ratio of fed HF to (fed HCC30+fed HCC20) was adjusted to about 2/1 and a molar ratio of fed HCC30 to fed HCC20 was varied to 100/0, 15/85 and 0/100. The reaction pressure was adjusted to 6 kg/cm²·G (gauge pressure). The reaction temperature was adjusted to 90° C. which is 5° C. higher than 85° C. (85° C. is the boiling point of HF at 6 kg/cm²·G (gauge pressure)), as the temperature where HF is not liquefied in the reaction liquid in case that the reaction pressure is 6 kg/cm²·G (gauge pressure). The concentration of $SbCl_xF_y$ in the reaction liquid was controlled to 50% by mol.

The reaction mixture was drawn from the reflux condenser and the reaction mixture was separated into a reaction product (a mixture of HFC32, HCFC22 and hydrogen chloride) and an unreacted material (a mixture of HCFC31, HCC30, HCFC21, HCC20 and HF). The drawn reaction mixture was introduced into a distillation column made of SUS-316 and was distilled at a pressure of 5 kg/cm²·G (gauge pressure). Then, the mixture of HFC32, HCFC22 and hydrogen chloride as the reaction product was mainly discharged from the distillation column condenser and the mixture of HCFC31, HCC30, HCFC21, HCC20 and HF as the main unreacted material was mainly drawn from the column bottom. The unreacted material was returned to the reactor to be recycled.

After the reaction between fed HCC30 and fed HCC20 in each molar ratio became stable, an organic substance and an acid contained in a reaction liquid, an outlet gas of the reflux condenser (with which the reactor is equipped), an outlet gas of the recycling device, and a recycled liquid were analyzed to determine the composition. The results are shown in Tables 1 to 3. The composition of $SbCl_xF_y$ used as the catalyst was determined by a quantitative analysis. As a result, y was about 1.2.

TABLE 1

| Composition | Reaction liquid (% by mol) | Condenser outlet gas (% by mol) | Recycling device outlet gas (% by mol) | Recycled liquid (% by mol) |
|---|---|---|---|---|
| HCl | | 47.5 | 66.5 | |
| HF | | 20.4 | 0.6 | 68.9 |
| HFC32 | | 24.3 | 32.2 | 4.4 |
| HCFC31 | 3.6 | 5.7 | 0.2 | 19.3 |
| HCC30 | 47.3 | 2.1 | | 7.4 |
| HCC40 | | 62 ppm | 87 ppm | |
| HFC23 | | | | |
| HCFC22 | | | | |
| HCFC21 | | | | |
| HCC20 | | | | |
| Sb catalyst | 49.1 | | | |

TABLE 2

| Composition | Reaction liquid (% by mol) | Condenser outlet gas (% by mol) | Recycling device outlet gas (% by mol) | Recycled liquid (% by mol) |
|---|---|---|---|---|
| HCl | | 45.7 | 66.5 | |
| HF | | 19.6 | 0.8 | 60.9 |
| HFC32 | | 3.4 | 5.0 | |
| HCFC31 | 0.6 | 3.7 | | 11.7 |
| HCC30 | 30.4 | | | |
| HCC40 | | 29 ppm | 43 ppm | |
| HFC23 | | 0.6 | 0.9 | |
| HCFC22 | 0.1 | 18.9 | 26.7 | 1.8 |
| HCFC21 | 2.6 | 8.0 | | 25.6 |
| HCC20 | 15.0 | | | |
| Sb catalyst | 51.3 | | | |

TABLE 3

| Composition | Reaction liquid (% by mol) | Condenser outlet gas (% by mol) | Recycling device outlet gas (% by mol) | Recycled liquid (% by mol) |
|---|---|---|---|---|
| HCl | | 43.7 | 65.7 | |
| HF | | 16.7 | 1.5 | 48.2 |
| HFC32 | | | | |
| HCFC31 | | | | |
| HCC30 | 5.2 | | | |
| HCC40 | | | | |
| HFC23 | | 1.1 | 1.6 | |
| HCFC22 | 3.2 | 27.5 | 30.9 | 18.5 |
| HCFC21 | 7.5 | 10.0 | 0.3 | 30.2 |
| HCC20 | 33.8 | 1.0 | | 3.1 |
| Sb catalyst | 50.3 | | | |

The above results show that the concentration of the catalyst in the liquid reaction mixture and y of the catalyst are stably controlled. Also, they show that the conversion of HCC30 and HCC20 in the recycling device outlet gas are very high such as at least 99% by mol and the amount of generated by-products is very small so that it is at most 0.1% by mol based on generated HFC32 and is at most 5% by mol based on generated HCFC22.

Example 2

Without using the device for recycling the unreacted material to the reactor in the apparatus of Example 1, the continuous fluorination reaction of HCC30 and HCC20 was conducted under the conditions of the temperature of 100° C. and the pressure of 6 kg/cm$^2$·G (gauge pressure). HCC30 (0.01 mol/minute), HCC20 (0.01 mol/minute) and HF (0.05 mol/minute) were continuously fed to the reactor and the reaction product was continuously drawn from the reflux condenser. The HF conversion, the HFC32 selectivity and the HCFC22 selectivity of the drawn reaction product were about 70% by mol, about 33% by mol and about 30% by mol, respectively. y of the catalyst was maintained at about 1 and the concentration of the catalyst in the reaction liquid was maintained at a constant (50% by mol). During this continuous fluorination, various metal pieces for material test, which were previously degreased with acetone and subjected to the measurement of the weight and size, were placed in the reaction liquid. The corrosion rate was determined by the measurement of the weight and the calculation of the surface loss of the metal pieces after 8 hours had passed. The results are shown in Table 4.

TABLE 4

| Type of material | Corrosion rate (mm/year) |
|---|---|
| Carbon steel | 1.04 |
| SUS-316 | 0.29 |
| Dual-phase stainless steel (DP-3) | 0.08 |
| NAR-25-50MTi | 0.01 or less |
| Hastelloy C-22 | 0.01 or less |

The results of Table 4 show that the metal material used usually in the reactor is not corroded excessively under the conditions of the present invention. However, the corrosion rate of the carbon steel is larger than that of the other materials.

Example 3

According to the same manner as in Example 2 except for changing the reaction temperature, the reaction was conducted. The temperature of 80° C. is the condition wherein HF is liquefied in the reaction liquid under the pressure of 6 kg/cm$^2$·G (gauge pressure), while the temperature of 120° C. is the condition wherein HF is not liquefied under the pressure of 6 kg/cm$^2$·G (gauge pressure). The results are shown in Table 5.

TABLE 5

| | Corrosion rate (mm/year) | |
|---|---|---|
| Type of material | 80° C. | 120° C. |
| Carbon steel | can not be measured because of severe corrosion | 1.26 |
| SUS-316 | can not be measured because of severe corrosion | 0.42 |
| Dual-phase stainless steel (DP-3) | 19.9 | 0.15 |
| NAR-25-50MTi | 21.3 | 0.01 or less |
| Hastelloy C-22 | 10.5 | 0.01 or less |

The results of Table 5 show that, when the reaction pressure is constant, the metal material used in the reactor is excessively corroded under the temperature condition where HF is liquefied but the corrosion is inhibited under the condition of the present invention where HF is not liquefied. Furthermore, the reaction product, y of the catalyst and the concentration of the catalyst in the reaction liquid could not be stably maintained under the condition where HF is liquefied.

Example 4

A carbon steel piece for material test, which was previously degreased with acetone and subjected to the measurement of the weight and size, was placed in a 100 mL container made of fluororesin. Then, $SbCl_xF_y$ (wherein y is 1) and HCC20 or HCC30 in a molar ratio of 1:1 were enclosed in the container and the reaction was conducted at the temperature of 80° C. The corrosion rate was determined by the weight measurement and the surface loss calculation of the carbon steel after 8 hours had passed. The results are shown in Table 6.

TABLE 6

| Type of material | Corrosion rate (mm/year) | |
|---|---|---|
| | HCC20 | HCC30 |
| Carbon steel | 0.58 | 1.41 |

As is apparent from Table 6, unfavorably, the carbon steel material used usually in the reactor is excessively corroded with HCC30 in comparison with HCC20.

EFFECT OF THE INVENTION

According to the present invention, HFC32 and HCFC22 can be simultaneously or alternatively produced in an efficient manner. Even in the reaction with antimony chloride fluoride and HF, which has high corrosiveness, the reactor made of the material such as Hastelloy C-22, NAR-25-50MTi hardly has corrosion. When the unreacted material is cycled, the conversion of HCC30, HCC20 and HF in the reaction system is very high and the amount of by-products generated in the reaction system is very small.

What is claimed is:
1. A process for producing difluoromethane and difluorochloromethane, which comprises reacting dichloromethane and trichloromethane in a liquid phase with hydrogen fluoride in a gas phase in the presence of a fluorinating catalyst in one reaction apparatus at a reaction pressure and temperature, wherein the reaction pressure is from 1 to 20 kg/cm², and the reaction temperature is within the range of from 50 to 150° C. and is a temperature at which hydrogen fluoride is not liquefied under the reaction pressure; and isolating the difluoromethane and difluorochloromethane products.

2. The process according to claim 1, wherein antimony chloride fluoride represented by the general formula:

$SbCl_xF_y$, wherein the sum of x and y is 5, is used as the fluorinating catalyst.

3. The process according to claim 2, wherein y is 0.5 to 2 in the general formula representing antimony chloride fluoride.

4. The process according to claim 1, wherein an amount of the fluorinating catalyst contained in a liquid reaction mixture is from 10 to 90% by mol based on the total amount of the reaction mixture and fluorinating catalyst.

5. The process according to claim 1, wherein the reaction temperature is adjusted to a temperature which is higher by at least 5° C. than a boiling point of hydrogen fluoride under the pressure.

6. The process according to claim 1, which comprises the steps of:
(1) charging a reaction mixture of dichloromethane, trichloromethane and hydrogen fluoride in a reactor to react in the presence of the fluorinating catalyst;
(2) drawing a part or all of the reaction mixture from the reactor;
(3) separating the drawn reaction mixture into a mixture mainly of difluoromethane, difluorochloromethane and hydrogen chloride as the reaction product and a mixture of other components;
(4) isolating difluoromethane and difluorochloromethane from the mixture of difluoromethane, difluorochloromethane and hydrogen chloride; and
(5) returning the mixture of other components obtained in the step (3) to the reactor.

7. The process according to claim 6, wherein the mixture of other components obtained in the step (3) is a mixture containing at least one selected from chlorofluoromethane, dichlorofluoromethane, dichloromethane, trichloromethane and hydrogen fluoride.

8. The process according to claim 6, which is continuously conducted.

9. The process according to claim 6, wherein the reactor is provided with a reflux column and a reflux condenser.

10. The process according to claim 1 or 6, wherein Hastelloy, NAR or dual-phase stainless steel is used as a material of the reactor.

11. The process according to claim 1, wherein difluoromethane and difluorochloromethane are produced alternatively in one reaction apparatus.

12. The process according to claim 1, wherein a molar ratio of hydrogen fluoride to the total of dichloromethane and trichloromethane fed into the reaction apparatus is from about 2:1 to 4:1.

13. The process according to claim 1, wherein y is 0.5 to 1.5 in the general formula representing antimony chloride fluoride.

14. The process according to claim 1, wherein an amount of the fluorinating catalyst contained in a liquid reaction mixture is from 40 to 70% by mol based on the total amount of the reaction mixture and fluorinating catalyst.

15. The process according to claim 1, wherein the reaction pressure is from 5 to 10 kg/cm².

16. The process according to claim 1, wherein a molar ratio of dichloromethane to trichloromethane fed into the reaction apparatus is from 1:100 to 100:1.

17. The process according to claim 1, wherein a molar ratio of hydrogen fluoride to the total of dichloromethane and trichloromethane fed into the reaction apparatus is from about 3:1 to 4:1.

18. A process for producing difluoromethane and difluorochloromethane, which consists essentially of reacting dichloromethane and trichloromethane with hydrogen fluoride in a liquid phase in the presence of a fluorinating catalyst in one reaction apparatus at a reaction pressure and temperature, wherein the molar ratio of dichloromethane to trichloromethane fed into the reaction apparatus is from 1:100 to 100:1, wherein the reaction pressure is from 1 to 20 kg/cm², and the reaction temperature is within the range of from 50 to 150° C. and is a temperature at which hydrogen fluoride is not liquefied under the reaction pressure; and isolating the difluoromethane and difluorochloromethane products.

19. The process according to claim 18, wherein antimony chloride fluoride represented by the general formula:

$$SbCl_xF_y,$$

wherein the sum of x and y is 5, is used as the fluorinating catalyst.

20. The process according to claim 19, wherein a molar ratio of hydrogen fluoride to the total of dichloromethane and trichloromethane fed into the reaction apparatus is from about 2:1 to 4:1.

* * * * *